(12) United States Patent
Eifion

(10) Patent No.: US 6,569,865 B2
(45) Date of Patent: May 27, 2003

(54) SPIRO 1-AZABICYCLO[2.2.2]OCTANE-3,2'(3'H)-FURO[2,3-B]PYRIDINE

(75) Inventor: Phillips Eifion, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/159,786

(22) Filed: May 31, 2002

(65) Prior Publication Data

US 2003/0018042 A1 Jan. 23, 2003

Related U.S. Application Data

(60) Provisional application No. 60/367,351, filed on Jun. 1, 2001.

(51) Int. Cl.$^7$ .................. C07D 405/14; A61K 31/47
(52) U.S. Cl. ............................. 514/278; 546/18
(58) Field of Search ............................ 546/18; 514/278

(56) References Cited

U.S. PATENT DOCUMENTS

| | | |
|---|---|---|
| 5,468,875 A | 11/1995 | Sabb et al. |
| 6,110,914 A | 8/2000 | Phillips et al. |

FOREIGN PATENT DOCUMENTS

| | | |
|---|---|---|
| WO | WO 96/06098 | 2/1996 |
| WO | WO 97/05139 | 2/1997 |
| WO | WO 98/54189 | 12/1998 |
| WO | WO 99/03859 | 1/1999 |
| WO | WO 00/42044 | 7/2000 |

OTHER PUBLICATIONS

Nordvall et al. "3–(2–Benzofuranyl)quinuclidin–2–ene Derivatives: Novel Muscarinic Antagonists" J Med Chem, vol. 39, 3269–3277 (1996).

Gregan et al. "Synthesis and locall anaesthetic activities of 3–(2–alkoxyphenylcarbamoyloxy)chinuclidinium chlorides" Pharmazie, 48, 465–466 (1993).

Nilsson et al. "Studies on carbanilic acid esters of cyclic amino alcohols" Acta Pharm. Suecica, 7, 239–246 (1970).

McDonald et al. "Nicotinic Acetylcholine Receptors: Molecular Biology, Chemistry and Pharmacology", chapter 5, in Annual Reports in Medicinal Chemistry, vol. 30, pp. 41–50, Academic Press Inc., San Diego. (1995).

Williams et al. "Neuronal Nicotinic Acetylcholine Receptors, Drug News and Perspectives", vol. 7, pp. 205–223 (1994).

*Primary Examiner*—Zinna Northington Davis
(74) *Attorney, Agent, or Firm*—Kenneth F. Mitchell

(57) ABSTRACT

A compound having the formula:

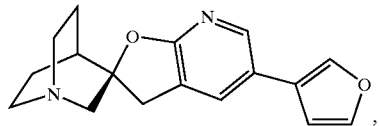

pharmaceutically-acceptable salts thereof, compositions containing them and uses thereof in therapy where activation of the $\alpha_7$ nicotinic receptor is beneficial.

14 Claims, No Drawings

SPIRO 1-AZABICYCLO[2.2.2]OCTANE-3,2' (3'H)-FURO[2,3-B]PYRIDINE

RELATED APPLICATIONS

This is a continuation of provisional U.S. application Ser. No. 60/367,351 having a filing date of Jun. 1, 2001, pending, converted from U.S. Utility application Ser. No. 09/871,773 having a filing date of Jun. 1, 2001.

TECHNICAL FIELD

This invention relates to a novel spiroazabicyclic heterocyclic amine or pharmaceutically acceptable salts thereof, processes for preparing them, pharmaceutical compositions containing them and their use in therapy. A further object is to provide active compounds that are potent ligands for nicotinic acetylcholine receptors (nAChR's).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; and in Williams et al. (1994) "Neuronal Nicotinic Acetylcholine Receptors," Drug News & Perspectives, vol. 7, pp. 205–223.

U.S. Pat. No. 5,468,875 discloses N-alkylcarbamic acid 1-azabicyclo[2.2.1]hept-3-yl esters, which are centrally active muscarinic agents useful in the treatment of Alzheimer's disease and other disorders.

N-(2-Alkoxyphenyl)carbamic acid 1-azabicyclo[2.2.2]octan-3-yl esters are disclosed in Pharmazie, vol. 48, 465–466 (1993) along with their local anesthetic activity. N-Phenylcarbamic acid 1-azabicyclo[2.2.2]octan-3-yl esters substituted at the ortho position on the phenyl ring are described as local anaesthetics in Acta Pharm. Suecica, 7, 239–246 (1970). Furopyridines useful in controlling synaptic transmission are disclosed in WO 97/05139.

Spiroquinuclidine furopyridines useful as acetylcholine agonists are disclosed in WO 99/03859.

SUMMARY OF THE INVENTION

The invention generally relates to a compound having the formula:

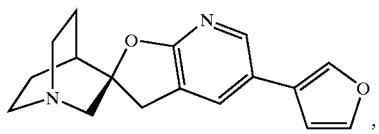

or a pharmaceutically-acceptable salt thereof, and their uses in therapy and compositions containing them.

DISCLOSURE OF THE INVENTION

One aspect of the invention is a compound having the formula:

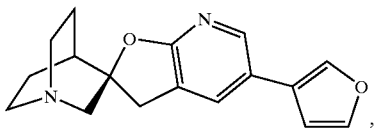

and any pharmaceutically-acceptable salts thereof.

Another aspect of the invention relates to a pharmaceutical composition comprising a compound as described above, and a pharmaceutically-acceptable diluent or carrier.

Another aspect of the invention relates to the above pharmaceutical composition for use in the treatment of prophylaxis of human diseases or conditions in which activation of the $\alpha_7$ nicotinic receptor beneficial.

Another aspect of the invention relates to the above pharmaceutical composition for use in the treatment or prophylaxis of psychotic disorders or intellectual impairment disorders.

Another aspect of the invention relates to the above pharmaceutical composition for use in the treatment or prophylaxis of Alzheimer's disease, learning deficit, cognition deficit, attention deficit, memory loss, Attention Deficit Hyperactivity Disorder, anxiety, schizophrenia, or mania or manic depression Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

Another aspect of the invention relates to a use of a compound as described above in the manufacture of a medicament for the treatment or prophylaxis of human diseases or conditions in which activation of the $\alpha_7$ nicotinic receptor is beneficial.

Another aspect of the invention relates to a use of a compound as described above in the manufacture of a medicament for the treatment or prophylaxis of psychotic disorders or intellectual impairment disorders.

Another aspect of the invention relates to the above use, wherein the condition or disorder is Alzheimer's disease, learning deficit, cognition deficit, attention deficit, memory loss, Attention Deficit Hyperactivity Disorder.

Another aspect of the invention relates to the above use, wherein the disorder is anxiety, schizophrenia, or mania or manic depression.

Another aspect of the invention relates to the above use, wherein the disorder is Parkinson's disease, Huntington's disease, Tourette's syndrome, or neurodegenerative disorders in which there is loss of cholinergic synapses.

Another aspect of the invention relates to the use of a compound as described above in the manufacture of a medicament for the treatment or prophylaxis of jetlag, cessation of smoking, nicotine addiction including that resulting from exposure to products containing nicotine, craving, pain, and for ulcerative colitis.

Another aspect of the invention relates to a method of treatment or prophylaxis of human diseases or conditions in which activation of the $\alpha_7$ nicotinic receptor is beneficial which comprises administering a therapeutically effective amount of a compound as described above.

Another aspect of the invention relates to a method of treatment or prophylaxis of psychotic disorders or intellectual impairment disorders, which comprises administering a therapeutically effective amount of a compound as described above.

Another aspect of the invention relates to the above method, wherein the disorder is Alzheimer's disease, learning deficit, cognition deficit, attention deficit, memory loss, or Attention Deficit Hyperactivity Disorder.

Another aspect of the invention relates to the above method, wherein the disorder is Parkinson's disease, Huntington's disease, Tourette's syndrome, or neurodegenerative disorders in which there is loss of cholinergic synapses.

Another aspect of the invention relates to the above method, wherein the disorder is anxiety, schizophrenia or mania or manic depression.

Another aspect of the invention relates to a method of treatment or prophylaxis of jetlag, cessation of smoking, nicotine addiction, craving, pain, and for ulcerative colitis, which comprises administering a therapeutically effective amount of a compound as described above.

Structurally related 5-aryl spirofuropyridines are described in WO 99/03859, for example the compounds of Example 3 and Example 21 (respectively, "Compound 1" and "Compound 2"). Relative to these compounds, the compounds of the present invention, and, in particular, the compound of Example 1 ("Compound 3"), possess surprisingly advantageous properties. In particular, as illustrated by the data in Table 1, the compound has the advantage of surprisingly enhanced potency in binding to the $\alpha_7$ nAChR, as well as enhanced selectivity versus the $\alpha_4$ receptor. The significantly greater potency and selectivity of Compound 3 result in advantageous properties that distinguish the compound's use as a pharmaceutical by lowering the efficacious dose, lengthening the duration of action, and improving side effect profile.

TABLE 1

| Compound | $\alpha_7$ binding ($\alpha_7$ Ki/nM) | nAChR Binding Selectivity (Ratio $\alpha_4$ Ki/$\alpha_7$ Ki) |
| --- | --- | --- |
| Compound 1 | 0.14 | 14000 |
| Compound 2 | 0.550 | 10000 |
| Compound 3 | 0.033 | 88000 |

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof or a pharmaceutically acceptable salt thereof, effective in treating or preventing such disorder or condition and an inert pharmaceutically acceptable carrier.

For the above-mentioned uses the dosage administered will, of course, vary with the compound employed, the mode of administration and the treatment desired. However, in general, satisfactory results are obtained when the compounds of the invention are administered at a daily dosage of from about 0.1 mg to about 20 mg/kg of animal body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
  for tablets and dragees: lactose, starch, talc, stearic acid;
    for capsules: tartaric acid or lactose;
  for injectable solutions: water, alcohols, glycerin, vegetable oils; for suppositories: natural or hardened oils or waxes.

There is also provided a process for the preparation of such a pharmaceutical composition which comprises mixing the ingredients.

Utility

A further aspect of the invention is the use of a compound according to the invention, an enantiomer thereof or a pharmaceutically acceptable salt thereof, in the manufacture of a medicament for the treatment or prophylaxis of one of the below mentioned diseases or conditions; and a method of treatment or prophylaxis of one of the above mentioned diseases or conditions, which comprises administering a therapeutically effective amount of a compound according to the invention, or an enantiomer thereof or a pharmaceutically acceptable salt thereof, to a patient.

Compounds according to the invention are agonists of nicotinic acetylcholine receptors. While not being limited by theory, it is believed that agonists of the $\alpha_7$ nAChR (nicotinic acetylcholine receptor) subtype should be useful in the treatment or prophylaxis of psychotic disorders and intellectual impairment disorders, and have advantages over compounds which are or are also agonists of the $\alpha_4$ nAChR subtype. Therefore, compounds which are selective for the $\alpha_7$ nAChR subtype are preferred. The compounds of the invention are indicated as pharmaceuticals, in particular in the treatment or prophylaxis of psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, craving, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for Affinity at α7 nAChR Subtype $_{125}$I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30–80 µg) were incubated with 5 nM $[^{125}I]$α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 μM (−)-nicotine, and specific binding was typically 75%.

Test B—Assay for Affinity to the $α_4$ nAChR Subtype

[$^3$H]-(−)-nicotine binding. Using a procedure modified from Martino-Barrows and Kellar (Mol Pharm (1987) 31:169–174), rat brain (cortex and hippocampus) was homogenized as in the [$_{125}$I]α-BTX binding assay, centrifuged for 20 minutes at 12,000×g, washed twice, and then resuspended in HB containing 100 μM diisopropyl fluorophosphate. After 20 minutes at 4° C., membranes (approximately 0.5 mg) were incubated with 3 nM [3H]-(−)-nicotine, test drug, 1 μM atropine, and either 2 mM $CaCl_2$ or 0.5 mM EGTA for 1 h at 4° C., and then filtered over Whatman glass fibre filters (thickness C) (pretreated for 1 h with 0.5% PEI) using a Brandel cell harvester. Nonspecific binding was described by 100 μM carbachol, and specific binding was typically 84%.

Binding Data Analysis for Tests A and B $IC_{50}$ values and pseudo Hill coefficients ($n_H$) were calculated using the non-linear curve-fitting program ALLFIT (DeLean A, Munson P J and Rodbard D (1977) Am. J. Physiol., 235:E97–E102). Saturation curves were fitted to a one site model, using the non-linear regression program ENZFITTER (Leatherbarrow, R. J. (1987)), yielding $K_D$ values of 1.67 and 1.70 nM for the $^{125}$I-α-BTX and [$^3$H]-(−)-nicotine ligands respectively. $K_i$ values were estimated using the general Cheng-Prusoff equation:

$$K_i = [IC_{50}]/((2+([ligand]/[K_D])_n)_{1/n} - 1)$$

where a value of n=1 was used whenever $n_H$<1.5 and a value of n=2 was used when $n_H$≧1.5. Samples were assayed in triplicate and were typically ±5%. $K_i$ values were determined using 6 or more drug concentrations. The compounds of the invention are compounds with binding affinities ($K_i$) of less than 1000 nM in either Test A or Test B, indicating that they are expected to have useful therapeutic activity.

The compounds of the invention have the advantage that they may be less toxic, be more efficacious, be longer acting, have a broader range of activity, be more potent, produce fewer side effects, are more easily absorbed or have other useful pharmacological properties.

EXAMPLES

Commercial reagents were used without further purification. Mass spectra were recorded using either a Hewlett Packard 5988A or a MicroMass Quattro-1 Mass Spectrometer and are reported as m/z for the parent molecular ion with its relative intensity. Room temperature refers to 20–25° C. The preparation of 5'-Bromospiro[1-azabicyclo[2.2.2]octane-3,2'(3'H)-furo[2,3-b]pyridine] and other precursors is described in patent application WO 99/03859.

Example 1

(2'R)-5'-(3-furanyl)spiro[1-azabicyclo[2.2.2]octane-3,2'(3'H)-furo[2,3-b]pyridine]

(2'R)-5'-bromo-spiro[1-azabicyclo[2.2.2]octane-3,2'(3'H)-furo[2,3-b]pyridine] (0.7 g, 2.37 mmol), 3-furylboronic acid (0.39 g, 3.5 mmol), tetrakis (triphenylphosphine)palladium (0) (131 mg, 0.11 mmol), and sodium carbonate (0.75 g, 7.1 mmol) were placed in a tube under nitrogen. Water (3 mL), ethanol (3 mL) and tetrahydrofuran (12 mL) were added. The mixture was then heated at 70° C. and stirred under nitrogen for 24 h. The mixture was then evaporated under vacuum and the residue from evaporation was partitioned between dilute aqueous sodium hydroxide and chloroform, the layers were separated, and the aqueous layer was further extracted with chloroform. The chloroform extract was dried (magnesium sulfate), filtered, and evaporated. The residue was purified by reverse phase HPLC on a Waters Novapak-HR $C_{18}$ Column using a gradient of 0–70% acetonitrile/water (each solvent containing 0.1% trifluoroacetic acid as a buffer) as the eluant. The product-containing fractions were evaporated, then the residue was dissolved in methanol. Excess concentrated hydrochloric acid was added, and the solution was evaporated to give the dihydrochloride salt of the title compound (489 mg) as a colourless solid; m.p. 223–225° C. (decomp.); m/z 283 (100%, MH+).

The radiolabelled version of Example 1 is useful in a screen for the discovery of novel medicinal compounds which bind to and modulate the activity, via agonism, partial agonism, or antagonism, of the alpha-7 nicotinic acetylcholine receptor. The particularly high potency of Example 1 in binding to the receptor is a particular advantage for radiolabelled Example 1 relative to radiolabelled structurally-related compounds, since the high potency would provide an advantage in the screen, by providing a high ratio of specific to non-specific binding. Radiolabelled Example 1 is synthesized either by the synthesis incorporating radiolabelled starting materials or, in the case of tritium, exchange of hydrogen in Example 1 for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

What is claimed is:

1. A compound having the formula:

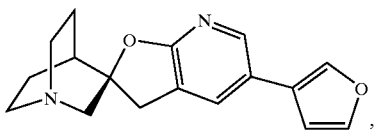

or a pharmaceutically-acceptable salt thereof.

2. A pharmaceutical composition comprising a compound according to claim 1, and a pharmaceutically-acceptable diluent or carrier.

3. The pharmaceutical composition according to claim 2, for use in the treatment of prophylaxis of human diseases or conditions in which activation of the $α_7$ nicotinic receptor is beneficial.

4. The pharmaceutical composition according to claim 2, for use in the treatment or prophylaxis of psychotic disorders or intellectual impairment disorders.

5. The pharmaceutical composition according to claim 2, for use in the treatment or prophylaxis of Alzheimer's disease, learning deficit, cognition deficit, attention deficit, memory loss, Attention Deficit Hyperactivity Disorder, anxiety, schizophrenia, mania, manic depression, Parkinson's disease, Huntington's disease, Tourette's syndrome, neurodegenerative disorders in which there is loss of cholinergic synapse, jetlag, cessation of smoking, nicotine addiction, craving, pain, and ulcerative colitis.

6. A method of treatment or prophylaxis of human diseases or conditions in which activation of the $\alpha_7$ nicotinic receptor is beneficial which comprises administering a therapeutically effective amount of a compound according to claim 1.

7. A method of treatment or prophylaxis of psychotic disorders or intellectual impairment disorders, which comprises administering a therapeutically effective amount of a compound according to claim 1.

8. The method according to claim 7, wherein the disorder is Alzheimer's disease, learning deficit, cognition deficit, attention deficit, memory loss, or Attention Deficit Hyperactivity Disorder.

9. The method according to claim 7, wherein the disorder is Parkinson's disease, Huntington's disease, Tourette's syndrome, or neurodegenerative disorders in which there is loss of cholinergic synapses.

10. The method according to claim 7, wherein the disorder is anxiety, schizophrenia or mania or manic depression.

11. A method of treatment or prophylaxis of jetlag, cessation of smoking, nicotine addiction, craving, pain, and for ulcerative colitis, which comprises administering a therapeutically effective amount of a compound according to claim 1.

12. A compound according to claim 1, wherein one or more of the atoms is labeled with a radioisotope of the same element.

13. A compound according to claim 12, wherein the radioisotope is tritium.

14. A method of using a compound according to claim 12, in a screen for the discovery of novel medicinal compounds which bind to and modulate the activity, via agonism, partial agonism, or antagonism, of the $\alpha_7$ nicotinic acetylcholine receptor.

* * * * *

UNITED STATES PATENT AND TRADEMARK OFFICE
CERTIFICATE OF CORRECTION

PATENT NO. : 6,569,865 B2
DATED : May 27, 2003
INVENTOR(S) : Eifion

It is certified that error appears in the above-identified patent and that said Letters Patent is hereby corrected as shown below:

Title page, Item [54] and Column 1, lines 1 and 2,
Title, "SPIRO 1-AZABICYCLO[2.2.2]OCTANE-3,2'-(3'h)-FURO[2,3-b] PYRIDINE" is corrected to read -- LIGAND FOR NICOTINIC ACETYLCHOLINE RECEPTORS --

Title page,
Item [12], "Eifion" is corrected to read -- Phillips --; and
Item [75], Inventor, "Phillips Eifion, Wilmington DE (US)" is corrected to read -- Eifion Phillips, Wilmington DE (US) --

Signed and Sealed this

Sixteenth Day of March, 2004

JON W. DUDAS
*Acting Director of the United States Patent and Trademark Office*